(12) United States Patent
Dam-Huisman

(10) Patent No.: US 11,998,180 B2
(45) Date of Patent: Jun. 4, 2024

(54) SYSTEM AND METHOD FOR ACTIVATING A SURGICAL INSTRUMENT, AND FOOT SWITCH ASSEMBLY FOR CONTROLLING A SURGICAL INSTRUMENT

(71) Applicant: Crea IP B.V., Vierpolders (NL)

(72) Inventor: Adriaantje Coliene Dam-Huisman, Delfgauw (NL)

(73) Assignee: Crea IP B.V., Vierpolders (NL)

( * ) Notice: Subject to any disclaimer, the term of this patent is extended or adjusted under 35 U.S.C. 154(b) by 0 days.

(21) Appl. No.: 17/625,364

(22) PCT Filed: Jul. 8, 2020

(86) PCT No.: PCT/NL2020/050447
§ 371 (c)(1),
(2) Date: Jan. 7, 2022

(87) PCT Pub. No.: WO2021/006734
PCT Pub. Date: Jan. 14, 2021

(65) Prior Publication Data
US 2022/0273275 A1    Sep. 1, 2022

(30) Foreign Application Priority Data
Jul. 9, 2019   (NL) ..................................... 2023465

(51) Int. Cl.
*A61B 17/00*   (2006.01)
*G05G 1/30*    (2008.04)
*H01H 3/14*    (2006.01)

(52) U.S. Cl.
CPC ............ *A61B 17/00* (2013.01); *G05G 1/305* (2013.01); *H01H 3/14* (2013.01); *A61B 2017/00371* (2013.01); *A61B 2017/00973* (2013.01)

(58) Field of Classification Search
CPC .......... A61B 17/00; A61B 2017/00371; A61B 2017/00973; G05G 1/305; H01H 3/14
(Continued)

(56) References Cited

U.S. PATENT DOCUMENTS

| 898,279 A | 9/1908 | Smith |
| 5,635,777 A | 6/1997 | Telymonde et al. |

(Continued)

FOREIGN PATENT DOCUMENTS

| JP | H04503913 A | 7/1992 |
| JP | 2012-183345 A | 9/2012 |

(Continued)

OTHER PUBLICATIONS

English language machine translation of Japanese Office Action for corresponding JP application No. 2022-500966 dated Feb. 16, 2024.

*Primary Examiner* — Aaron F Roane
(74) *Attorney, Agent, or Firm* — N.V. Nederlandsch Octrooibureau

(57) ABSTRACT

System (20) with a safety lock (21), the safety lock (21) being configured to at least partially prevent use of a surgical instrument (22). A foot switch assembly (1) is operably configured to control the surgical instrument (22), and has multiple switches (4; 10; 14; 15; 16). A memory (26) is present for storing a predetermined switch sequence associated with the switches (4; 10; 14; 15; 16) of the foot switch assembly (1), as well as a control unit (25) configured to determine whether a series of input switch actuations from the foot switch assembly (1) corresponds to the predetermined switch sequence, and if so, deactivating the safety lock (21) in response to the series of input switch actuations corresponding to the predetermined switch sequence. The invention also relates to various embodiments of a foot switch assembly for controlling a surgical instrument.

5 Claims, 3 Drawing Sheets

(58) Field of Classification Search
USPC .............................................................. 606/4
See application file for complete search history.

(56) References Cited

U.S. PATENT DOCUMENTS

| | | | |
|---|---|---|---|
| 11,464,565 B2 * | 10/2022 | Jawidzik | G01V 8/20 |
| 2003/0047434 A1 * | 3/2003 | Hanson | G05G 1/30 |
| | | | 200/86.5 |
| 2004/0035242 A1 | 2/2004 | Peterson et al. | |
| 2006/0145540 A1 | 7/2006 | Mezhinsky | |
| 2010/0198200 A1 | 8/2010 | Horvath | |
| 2014/0364864 A1 | 12/2014 | Lynn et al. | |

FOREIGN PATENT DOCUMENTS

| | | |
|---|---|---|
| WO | WO90/09141 A2 | 8/1990 |
| WO | WO2020/039349 A1 | 3/2008 |

\* cited by examiner

SYSTEM AND METHOD FOR ACTIVATING A SURGICAL INSTRUMENT, AND FOOT SWITCH ASSEMBLY FOR CONTROLLING A SURGICAL INSTRUMENT

TECHNICAL FIELD

The present invention relates to a system and a method for activating a surgical instrument in a first aspect. In a further aspect, the present invention relates to a foot switch assembly for controlling a surgical instrument, in particular ophthalmic surgical instruments.

BACKGROUND OF THE INVENTION

During many surgical procedures, a surgeon or health care professional may employ many hand held instruments for treating, excising, or manipulating tissue. Fine control of such instruments and target tissue is often required in confined spaces, especially during ophthalmic surgery. Many ophthalmic surgical instruments have several modes of operation, and implementing manual controls on the body of such instruments is not practical, especially with small gauge instruments, nor is it always convenient to place controls on hand-held instruments that require fine motor control during use.

Control panels or systems for activating, deactivating and controlling multiple functions of a surgical instruments are often provided remote from the hand-held portion of the instrument. However, the control panels and associated user interfaces are preferably manipulated in an intuitive manner with an available body part of the operation of the surgical instrument.

In this context, foot switch assemblies for controlling surgical instruments and systems have become a popular choice for controlling surgical instruments and associated observation instruments. Foot switch assemblies can be intuitively operated by the user, have the potential to support multiple input switches, and can exploit the range of movement and fine control exhibited by the user's foot.

Foot switches for controlling ophthalmic surgical instruments and systems are known in the art. For example, American patent publication U.S. Pat. No. 7,019,234 describes a foot switch intended as a controller for use during a surgical procedure. The foot switch can have a treadle having a slidable plate that facilitates the actuation of a side switch.

However, known foot switches have a number of draw backs that can impair the user experience, make the pedals counter intuitive to use, and result in sub-optimal control of the instruments or system that the foot switch is designed to control.

US patent publication US2014/364864 discloses a foot pedal system and apparatus with multiple switches. The foot pedal may include a housing and comprises at least one potentiometer and at least two top switches, and a treadle rotatably mounted within the housing and suitable for depressing the at least one potentiometer, and at least two side switches movably associated with the treadle. The treadle rotates horizontally over an axis which is located remote from the heel rest.

US patent publication US2006/014554 discloses a foot switch with a tiltable treadle for a first linear control input, which enables a second linear control input by use of a radial slider assembly positioned on top of the pedal treadle. Movement of the radial slider assembly provides a second linear control input to a potentiometer. The radial slider has a virtual pivoting axis located near the heel rest. The treadle has a rotating axis remote from the heel rest.

SUMMARY OF THE INVENTION

The present invention embodiments seek to provide a system and method for operating a foot pedal assembly, which allows proper, reliable and intuitive operation of a surgical instrument.

In a first aspect of the invention a method for activating a surgical instrument, the method comprising the steps of providing an apparatus having a safety lock, the safety lock being configured to prevent use of the surgical instrument, providing a foot switch assembly operably configured to control the surgical instrument, the foot switch assembly comprising multiple switches, storing, in a memory, a predetermined switch sequence associated with the switches of the foot switch assembly, determining whether a series of input switch actuations corresponds to the predetermined switch sequence, and if so, deactivating the safety lock in response to the series of input switch actuations corresponding to the predetermined switch sequence. Furthermore, a system is provided comprising a safety lock, the safety lock being configured to at least partially prevent use of a surgical instrument, a foot switch assembly operably configured to control the surgical instrument, the foot switch assembly comprising multiple switches, a memory storing a predetermined switch sequence associated with the switches of the foot switch assembly, a control unit configured to determine whether a series of input switch actuations from the foot switch assembly corresponds to the predetermined switch sequence, and if so, deactivating the safety lock in response to the series of input switch actuations corresponding to the predetermined switch sequence. In these embodiments it is possible to implement a safety lock feature in a system using a foot pedal switch assembly without a physical shroud to over the actuation surfaces of the foot switch to prevent (or minimise the risk of) unintended activation of a potentially hazardous function (e.g. activation of a laser). By preventing activation of the laser until a pre-defined switch sequence input, it is possible to provide a shroud function without using a physical locking/unlocking mechanism such as a brace or other constructional feature.

In a further aspect of the present invention, a foot switch assembly for controlling a surgical instrument is provided, the foot switch assembly comprising a base extending from a forward end to a rear end, said foot switch assembly comprising a heel rest at the rear end of the base, said heel rest having an upper surface, optionally a substantially flat upper surface. A moveable foot pedal is positioned adjacent to the heel rest, wherein the foot pedal is mounted to the base via a hinge having a pivot axis, and wherein the pivot axis of the moveable foot pedal relative to the heel rest centred with respect to the upper surface of the heel rest. By providing a foot switch assembly according to the first aspect, it is possible to provide a foot switch assembly that allows a comfortable and intuitive operational use of the foot pedal and the associated functions, in a manner that prevents any undesired or unwanted sliding of the foot over the foot pedal surface during actual use. The heel rest can be fixed, or the heel rest can be configured to rotate about a vertical axis (or a near vertical axis). A heel rest configured to rotate about a vertical axis can provide an additional range of movement without requiring the user to rotate their heel relative to the heel rest.

Preferred embodiments are described in the appended dependent claims, as well as with reference to the drawings showing exemplary embodiment of the present invention.

BRIEF DESCRIPTION OF THE FIGURES

The invention will now be described with reference to a number of non-limiting exemplary embodiment as illustrated in the enclosed drawings in which.

DETAILED DESCRIPTION OF THE DRAWINGS

The preferred embodiments of the invention and the associated advantages will be best understood by referring to FIGS. 1-5, in combination with the detailed description below. It will be understood that the following description relates to a number of non-limiting exemplary embodiments of the invention. Modifications and variations may be made to the following exemplary embodiment without departing from the scope of the claims.

Figure 1:
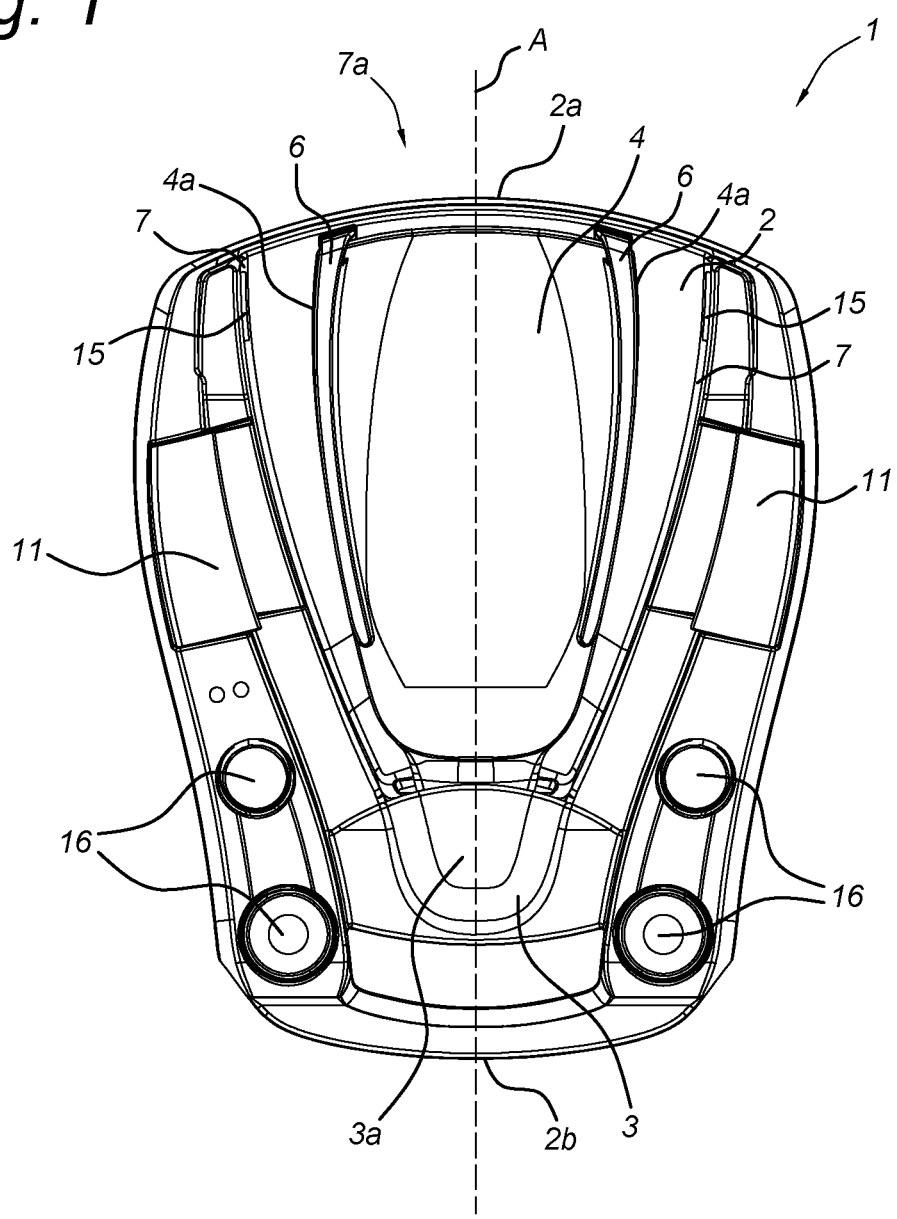
FIG. 1 shows a plan view of a foot switch assembly according to an embodiment of the invention.
Figure 2:
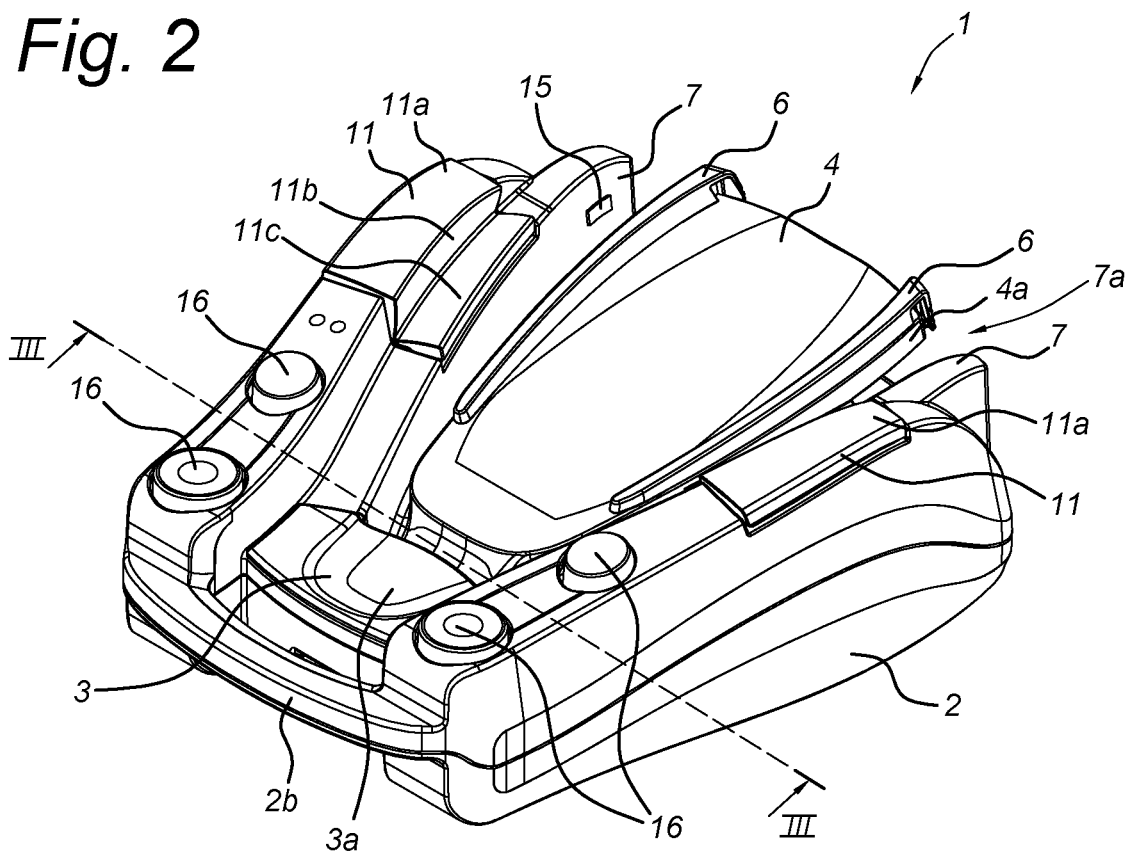
FIG. 2 shows a perspective view of the foot switch assembly shown in FIG. 1.

FIG. 1 shows a plan (top) view of a foot switch assembly 1 according to an embodiment of the invention, and FIG. 2 shows a perspective view of the embodiment of the foot switch assembly. As shown in FIGS. 1 and 2, the foot switch assembly 1 generally comprises a base 2 and a foot pedal 4 moveably mounted to the base 2. The base 2 extends from a forward end 2a to a rear end 2b, on which the moveable foot pedal 4 is mounted. The base 2 further comprises opposing sides semi-symmetrically extending between the forward and rear ends 2a, 2b of the base 2. The moveable foot pedal 4 is mounted to the base using a hinge 5, the details of which will be explained in further detail with reference to FIG. 4 below. The moveable foot pedal 4 is mounted in front of a heel rest 3 at the rear end 2b of the base 2, such that during use, the heel of a foot of an operator can rest on the heel rest 3, allowing actuation of the moveable foot pedal 4 by the rest of the foot of the user easily and comfortably.

In alternative wording, the present invention embodiments, in a first aspect, relate to a foot switch assembly 1 for controlling an ophthalmic surgery apparatus, the foot switch assembly 1 comprising a base 2 extending from a forward end 2a to a rear end 2b, said foot switch assembly 1 comprising a heel rest 3 at the rear end 2b of the base 2 with an upper surface 3a, and a moveable foot pedal 4 positioned adjacent to the heel rest 3, wherein the foot pedal 4 is mounted to the base 2 via a hinge 5 having a pivot axis $A_y$, $A_h$, and wherein the pivot axis $A_y$, $A_h$ of the moveable foot pedal 4 relative to the heel rest 3 is centred with respect to the upper surface 3a of the heel rest 3. The heel rest can be fixed, or it may be configured to rotate about a vertical axis. Advantageously, the upper surface of the heel rest is restricted to movement in a single plane (e.g. the heel rest can rotate about a vertical axis, but not around a horizontal axis). Translational movement of the heel rest relative to the base is preferably prevented. Such a configuration can provide a stable surface on which the heel can rest during operation of the switch.

The upper surface of the heel rest may be substantially flat, it may comprise a slightly concave or convex curvature, and/or additional surface features, such as grooves or ridges to minimise the likelihood of the user's foot slipping relative to the heel rest.

In an embodiment of the foot switch assembly 1 according to the present invention, the base 2 further comprises a channel 7a extending in a forward-backward direction, the channel 7a being defined by opposing side walls 7, and the foot pedal 4 being disposed within the channel 7a between the opposing side walls 7. As shown in FIGS. 1 and 2, the base 2 comprises a channel 7a configured to receive a user's foot. The channel 7a extends from a heel receiving portion located at the rear end 2b of the base 2, towards a toe receiving portion located at the forward end 2a of the base 2. Advantageously, the channel 7a may taper from the wider toe receiving portion to a narrower heel receiving portion (i.e. near the heel rest 3). However, it will be appreciated that the foot switch may be configured without a tapered channel.

The moveable foot pedal 4 is mounted within the channel 7a and is pivotally arranged with respect to the base 2. The foot pedal 4 is mounted to the base 2 as is described in further detail with reference to FIG. 4 below. The foot pedal 4 is configured such that its pivot axis $A_y$, $A_h$ extends in the same plane as the upper (flat) surface 3a of the heel support 3. By configuring the pivot point and the foot pedal 4 in this manner, the pivot axis $A_y$, $A_h$ of the foot pedal 4 during use extends through the point at which the user's heel contacts the upper surface 3a of the heel rest 3. This ensures that the user's foot does not slide up and down the foot pedal 4 as the user raises and lowers the foot to operate the foot pedal 4. By preventing movement of the foot relative to the surface of the foot pedal 4 during a pivoting motion of the foot about the heel, the chance of the user's foot slipping with respect to the surface of the foot pedal 4 is greatly reduced.

The base 2 may further comprise a number of additional switches or actuators. For example, as shown in FIG. 1 additional switches 16 are present at the top surface of the base 2 near the rear end 2b, which can e.g. be easily operated by a user's foot before it is positioned on the foot pedal 4. Additionally or alternatively, the foot switch assembly 1 further comprises a left and a right front pedal switch 15, operable by respective left and right side surfaces 4a of the foot pedal 4, as shown in the exemplary embodiment shown in FIGS. 1 and 2.

Also shown in the exemplary embodiment of FIGS. 1 and 2 are optionally present width limiters 6. The foot switch assembly 1 may further comprise one or more adjustable width limiters 6 on a top surface of the foot pedal 4 to enable a tight fitting of a user's foot on the foot pedal 4, allowing for comfortable movement of the foot pedal 4 not only up and down, but also in a sideways manner. The adjustable width limiters 6 are e.g. implemented as elongated strips, pivotally connected to the foot pedal 4 at an end near the heel rest 3, and fixable in a number of pre-set positions at a far end of the foot pedal 4 (i.e. near the forward end 2a of the base 2). The skilled person will appreciate that other width-adjusting configurations are also possible. For example, the elongate strips may be replaced with a series of discrete projections that extend inwardly from the outer edge of the movable pedal. Each of these projections may be slidably mounted with respect to the movable pedal, towards and away from the longitudinal centre line of the pedal. Such projections may be adjusted to closely surround the foot of a user. Other possible configurations will be apparent to the skilled person.

Figure 3:
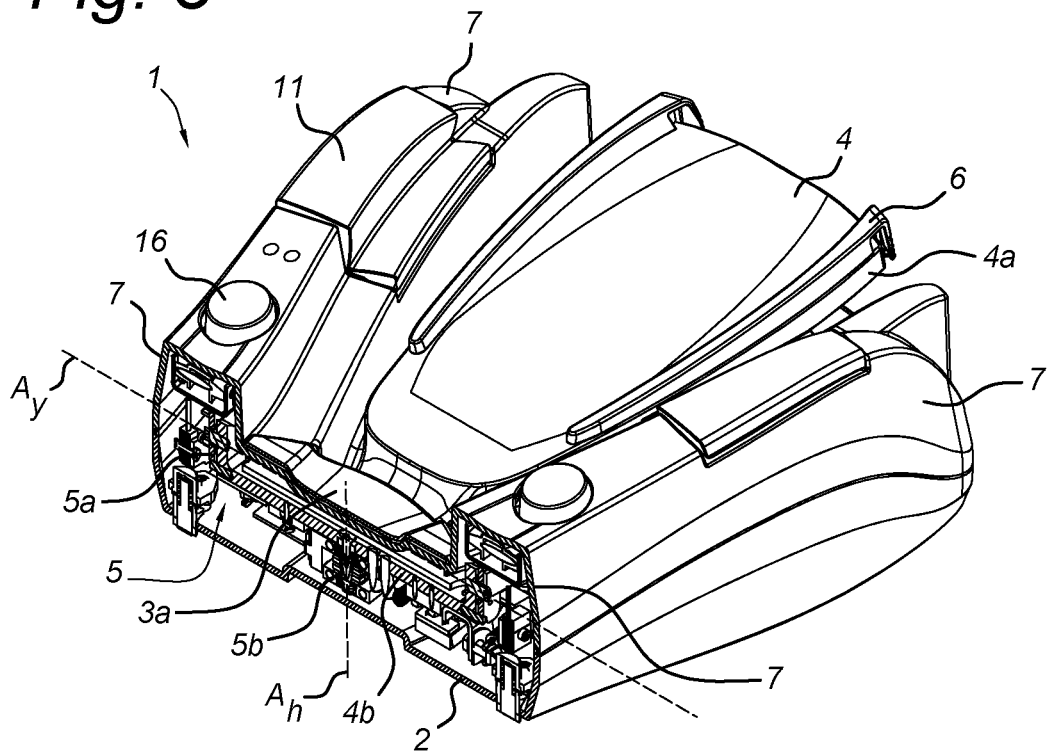
FIG. 3 shows a cross-sectional view of the foot switch assembly shown in FIG. 1 along line A-A.

FIG. 3 shows a cross-sectional view of the foot switch assembly shown in FIG. 1 along line A-A. In this cross sectional view further features relating to the pivot axes $A_y$, $A_h$ of the moveable foot pedal 4 obtained by specific structure embodiments of the hinge 5, which can comprise a first (vertical) hinge assembly 5a and/or a second (horizontal) hinge assembly 5b, are shown and described in further detail. In a first group of embodiments, the hinge 5 comprises a first hinge assembly 5a for allowing rotation of the moveable foot pedal 4 around a first hinge axis $A_y$, the first hinge axis $A_y$ extending parallel to and substantially coinciding with the upper surface 3a of the heel rest 3. In an exemplary embodiment, the first hinge axis $A_y$ is positioned very close to the upper surface 3a of the heel rest 3, e.g. within 30 mm. This embodiment allows the foot pedal 4 to move up and down, e.g. to provide a switch signal or a proportional control signal to a connected surgical instrument, using an appropriate switch or transducer, etc. A travel of the moveable foot pedal 4 in vertical direction is less than 15°, e.g. equal to 11°, in a further embodiment.

In addition (or alternatively), the hinge 5 may comprises a second hinge assembly 5b for allowing rotation of the moveable foot pedal 4 around a second hinge axis $A_h$, the second hinge axis $A_h$ extending substantially perpendicular to the upper surface 3a of the heel rest 3. This implementation of the hinge 5 with hinge assemblies 5a and 5b allows the foot pedal 4 to move left and right in the foot switch assembly 1. A travel of the moveable foot pedal 4 in horizontal direction can be between −10° and 10°, e.g. between −6.5° and 6.5°. Again, an appropriate position transducer or a switch may be used in combination with this implementation of the hinge 5 to provide a corresponding actuation signal to the surgical instrument. It is noted that in the embodiment shown in FIG. 3, the hinge 5 has a combination of a vertical and horizontal hinge assembly 5a, 5b with hinge axes $A_y$, $A_h$, respectively, allowing the foot pedal 4 to move up and down, and left and right in the channel 7a of the foot pedal assembly 1.

In the exemplary embodiment shown in FIG. 3, the foot pedal 4 comprises a foot pedal attachment assembly 4b (as an integral part of the foot pedal 4). The foot pedal attachment assembly 4b is connected to the base 2 such that the virtual axis about which the pedal rotates is located beneath a center point of the upper surface 3a of the heel rest 3. The pivotable connection is in this exemplary embodiment implemented by the horizontal hinge assembly 5b. This may be a bearing assembly or another low friction pivotable connection as will be apparent to the person skilled in the art in light of the present disclosure. Furthermore, the foot pedal attachment assembly 4b comprises two arm elements which extend sideways in an inner space of the base 2, such that the vertical hinge assembly 5a can be implemented at the correct height to have the associated vertical hinge axis $A_y$ coincide with the upper surface 3a of the heel rest 3.

Figure 4:
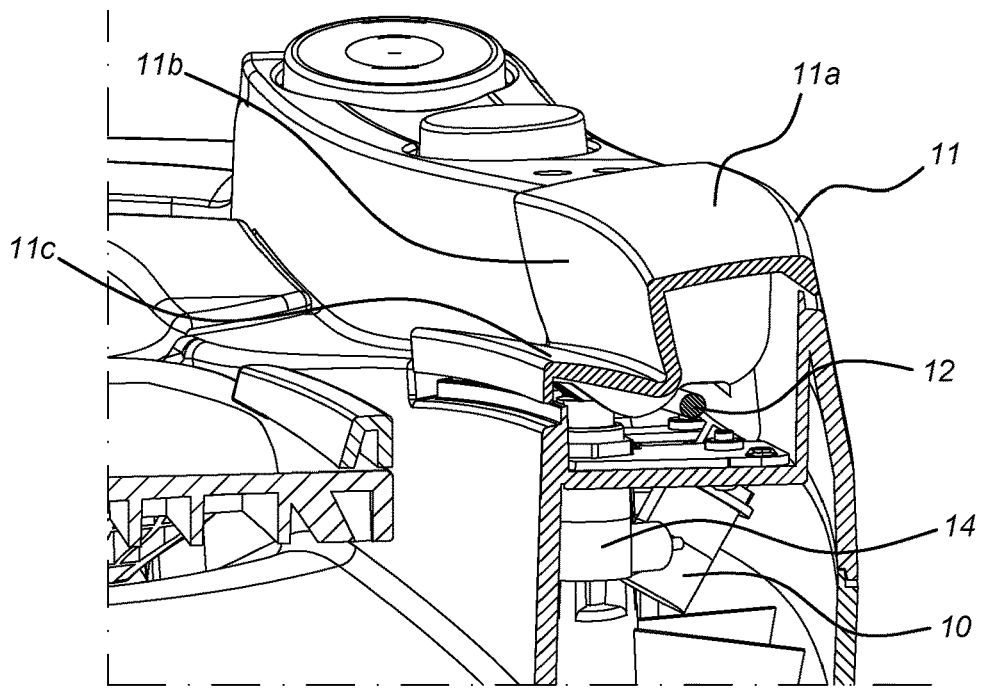
FIG. 4 shows an enlarged cross-sectional view of a part of the foot switch assembly shown in FIG. 1, showing an embodiment of the multi-actuation switch embodiments.

FIG. 4 shows an enlarged cross-sectional view of a part of the foot switch assembly 1 shown in FIGS. 1 and 2, showing an embodiment of the foot switch assembly having a multi-actuation switch 10. In this embodiment, the multi-actuation switch 10 is operable by an actuation body 11 with a pivot axis 12 extending substantially parallel to the moveable foot pedal 4 (i.e. perpendicular to the cross sectional face shown in FIG. 4). The actuation body 11 comprises two actuation surfaces 11a, 11b substantially perpendicular to each other and extending along the pivot axis 12. The actuation body 11 is arranged to operate the multi-actuation switch 10 by rotation over the pivot axis 12 in a first direction. Note that in FIG. 4 a single actuation body and multi-action switch 10 are shown, but from the exemplary FIGS. 1 and 2 embodiments it is clear that such switch arrangements can be present on both sides of the foot switch assembly 1. The upper one 11a of the actuation surfaces 11a, 11b can e.g. be operated by a user directly when the foot is not resting on the heel rest 3 and foot pedal 4, or when the foot is solely resting on the heel rest 3 (and not on the foot pedal 4). The directly connected side one 11b of the actuation surfaces 11a, 11b, can be operated easily by an operator by raising the foot from the foot pedal 4 but at the same time keeping the heel at the heel rest 3.

In an even further embodiments, the foot switch assembly 1 further comprises a second switch 14, wherein the actuation body 11 further comprises a second actuation surface 11c extending along the pivot axis 12, the second switch 14 being operable by rotating the actuation body 11 over the pivot axis 12 in a second direction opposite to the first direction. This embodiment e.g. allows to add an additional switch action which is clearly discernible over a switch action using one of the actuation surfaces 11a, 11b as described in the previous paragraph, because of the different actuation directions.

Discernible and more intuitive actuation can be achieved as a further enhancement in a further embodiment, wherein the second actuation surface 11c and one of the two actuation surfaces 11a, 11b adjacent to the pivot axis 12 form an angle of less than 90 degrees. This will ensure that the second actuation surface 11c extends from the base 2 after earlier actuation of the multi-action switch 10, allowing an easier 'back' action for actuation of the second switch 14.

Figure 5:
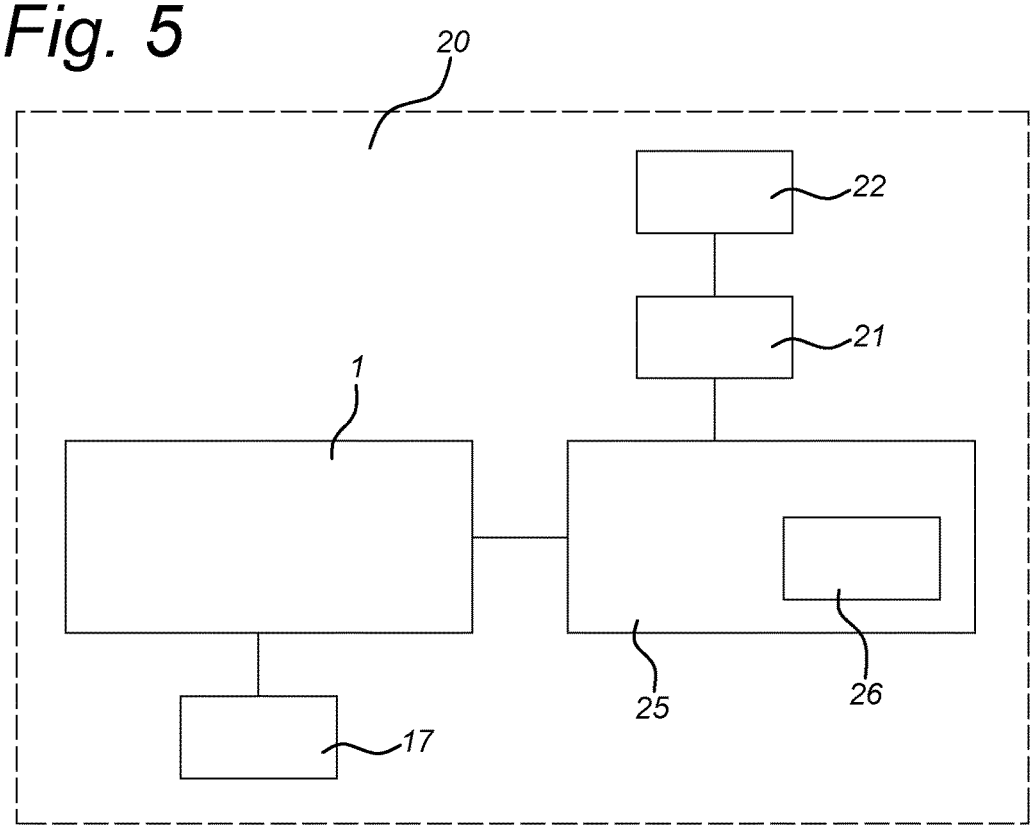
FIG. 5 shows a block diagram of a system embodiment according to an embodiment of the present invention.

FIG. 5 shows a block diagram of a system embodiment of the present invention, relating to a system 20 comprising a safety lock 21, the safety lock 21 being configured to at least partially prevent use of a surgical instrument 22. A foot switch assembly 1 is present as well and operably configured to control the surgical instrument 22. As in one or more of the exemplary embodiments described above, the foot switch assembly 1 comprises multiple switches 4; 10; 14; 15; 16. A memory 26 is present for storing a predetermined switch sequence associated with the switches 10; 14; 15; 16 of the foot switch assembly 1, as well as a control unit 25 configured to determine whether a series of input switch actuations from the foot switch assembly 1 corresponds to the predetermined switch sequence, and if so, deactivating the safety lock 21 in response to the series of input switch actuations corresponding to the predetermined switch sequence. This allows to provide a control arrangement for a surgical instrument, such as an ophthalmic surgical instrument, without a physically present protection shroud, as the sequence of switch actions (indicating presence of the foot of a user and intent of the user to actually use the instrument) can be used to switch off the safety lock 21.

In an exemplary embodiment, the surgical instrument 22 comprises a laser device controlled by an ophthalmic surgery instrument to which the foot switch assembly 1 is operably connected. Of course, a laser device should never be in operation unintentionally and this embodiment can make sure that the laser device is only active when the user actually wants the laser device to be active.

In an even further embodiment of the system 20, or as an even further embodiment of the foot switch assembly 1 described above, additional security preventing inadvertent operation of a surgical instrument is provided. To that end, the foot switch assembly 1 further comprise one or more sensor 17 for detecting presence of a foot of a user on the foot pedal 4. The sensor(s) 17 can comprise a weight sensor, an optical sensor, a capacitive sensor, etc. A plurality of sensors of different types may also be provided.

Depending on which type of surgical instrument is to be actuated using the present foot pedal assembly 1, the sensor signal can be used to initially or eventually actuate the surgical instrument, and if present, release the safety lock 21. E.g. if the surgical instrument is a laser device, a ready status of the laser device is only activated by the control unit 25 if a weight is detected by the weight sensor 17.

It is noted that different types of surgical instruments may be activated using the system 20 embodiments as described in combination with one of the foot pedal assembly embodiments described above, which enables a fail-safe operation of the surgical instrument at all times. In general terms, in a further invention aspect a method is provided for activating a surgical instrument (e.g. an ophthalmic instrument), the method comprising providing an apparatus having a safety lock, said safety lock being configured to prevent use of the instrument, providing a foot switch assembly 1 operably configured to control the surgical instrument, the foot switch assembly 1 comprising multiple switches 10; 14; 15; 16. Furthermore, the method comprises storing, in a memory 26, a predetermined switch sequence associated with the switches 10; 14; 15; 16 of the foot switch assembly 1, and determining whether a series of input switch actuations corresponds to the predetermined switch sequence. If so, the method further comprises deactivating the safety lock in response to the series of input switch actuations corresponding to the predetermined switch sequence.

The present invention has been described above with reference to a number of exemplary embodiments as shown in the drawings. Modifications and alternative implementations of some parts or elements are possible, and are included in the scope of protection as defined in the appended claims.

The invention claimed is:

1. A system comprising
    a safety lock, the safety lock being configured to at least partially prevent use of a surgical instrument;
    a foot switch assembly operably configured to control the surgical instrument, the foot switch assembly comprising multiple switches;
    a memory storing a predetermined switch sequence associated with the multiple switches of the foot switch assembly;
    a control unit configured to determine whether a series of input switch actuations from the foot switch assembly corresponds to the predetermined switch sequence, and if so, deactivating the safety lock in response to the series of input switch actuations corresponding to the predetermined switch sequence.

2. The system according to claim 1, wherein the surgical instrument comprises a laser device controlled by an ophthalmic surgery instrument to which the foot switch assembly is operably connected.

3. The system according to claim 1, wherein the foot switch assembly further comprises a sensor configured to detect presence of a foot of a user on the moveable foot pedal.

4. The system according to claim 3, wherein a ready status of the surgical instrument is only activated if a foot is detected by the sensor.

5. A method for activating a surgical instrument, the method comprising:
    providing an apparatus having a safety lock, the safety lock being configured to prevent use of the surgical instrument;
    providing a foot switch assembly operably configured to control the surgical instrument, the foot switch assembly comprising multiple switches;
    storing, in a memory, a predetermined switch sequence associated with the multiple switches of the foot switch assembly;
    determining whether a series of input switch actuations corresponds to the predetermined switch sequence, and if so, deactivating the safety lock in response to the series of input switch actuations corresponding to the predetermined switch sequence.

* * * * *